United States Patent [19]

Batina et al.

[11] Patent Number: 4,586,508
[45] Date of Patent: May 6, 1986

[54] IMPLANT COMMUNICATION SYSTEM WITH PATIENT COIL

[75] Inventors: William P. Batina; Lamar H. Gipson, both of Miami, Fla.

[73] Assignee: Cordis Corporation, Miami, Fla.

[21] Appl. No.: 592,959

[22] Filed: Mar. 23, 1984

[51] Int. Cl.$^4$ .............................................. D61N 1/36
[52] U.S. Cl. ................. 128/419 PG; 128/903
[58] Field of Search ............... 128/419 PG, 419 PS, 128/419 PT, 419 C, 419 E, 419 F, 697, 903, 631

[56] References Cited

U.S. PATENT DOCUMENTS

| | | | |
|---|---|---|---|
| 3,426,748 | 2/1969 | Bowers | 128/419 PG |
| 3,650,276 | 3/1972 | Burghele et al. | 128/419 E |
| 4,230,120 | 10/1980 | McDonald | 128/419 PT |
| 4,281,664 | 8/1981 | Duggan | 128/419 PT |
| 4,361,153 | 11/1982 | Slocum et al. | 128/419 PT |

OTHER PUBLICATIONS

Medtronic, Inc. Publication No. M4041-3/69049A1 1969, 42 pp.

Primary Examiner—William E. Kamm
Attorney, Agent, or Firm—George H. Gerstman

[57] ABSTRACT

A system is provided for communicating with a tank circuit that is implanted in a patient. The system comprises a telemetry circuit including an oscillator enclosed within a housing. An inductor coil is located outside of the housing for positioning externally on the patient in proximity to the implanted tank circuit. The inductor coil is connected to the telemetry circuit by electrical wiring, with the inductor coil being operative to form at least a portion of a resonant tank for the oscillator.

11 Claims, 11 Drawing Figures

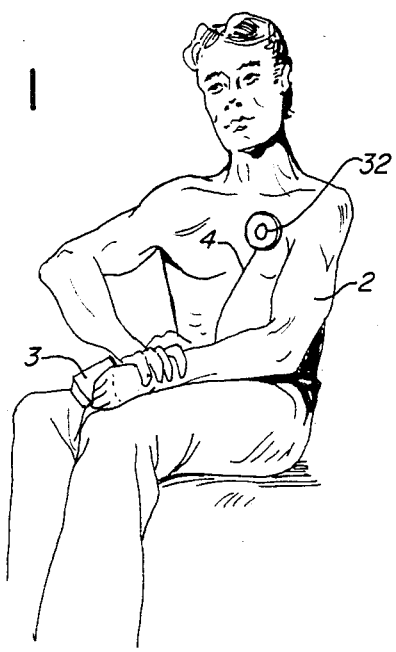
FIG. 1
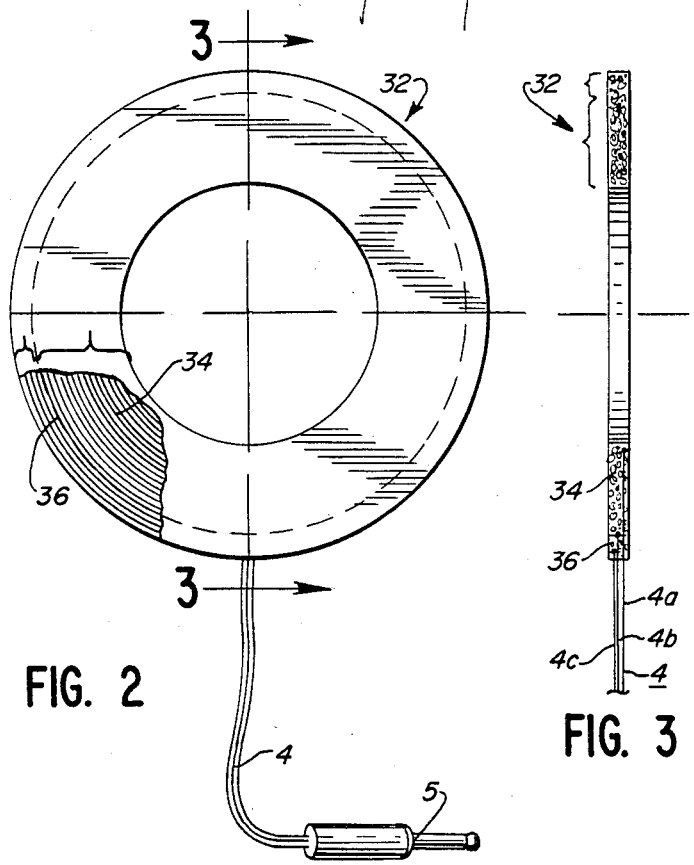
FIG. 2
FIG. 3
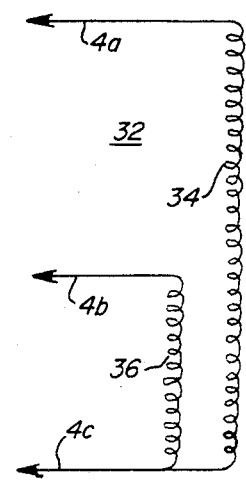
FIG. 4

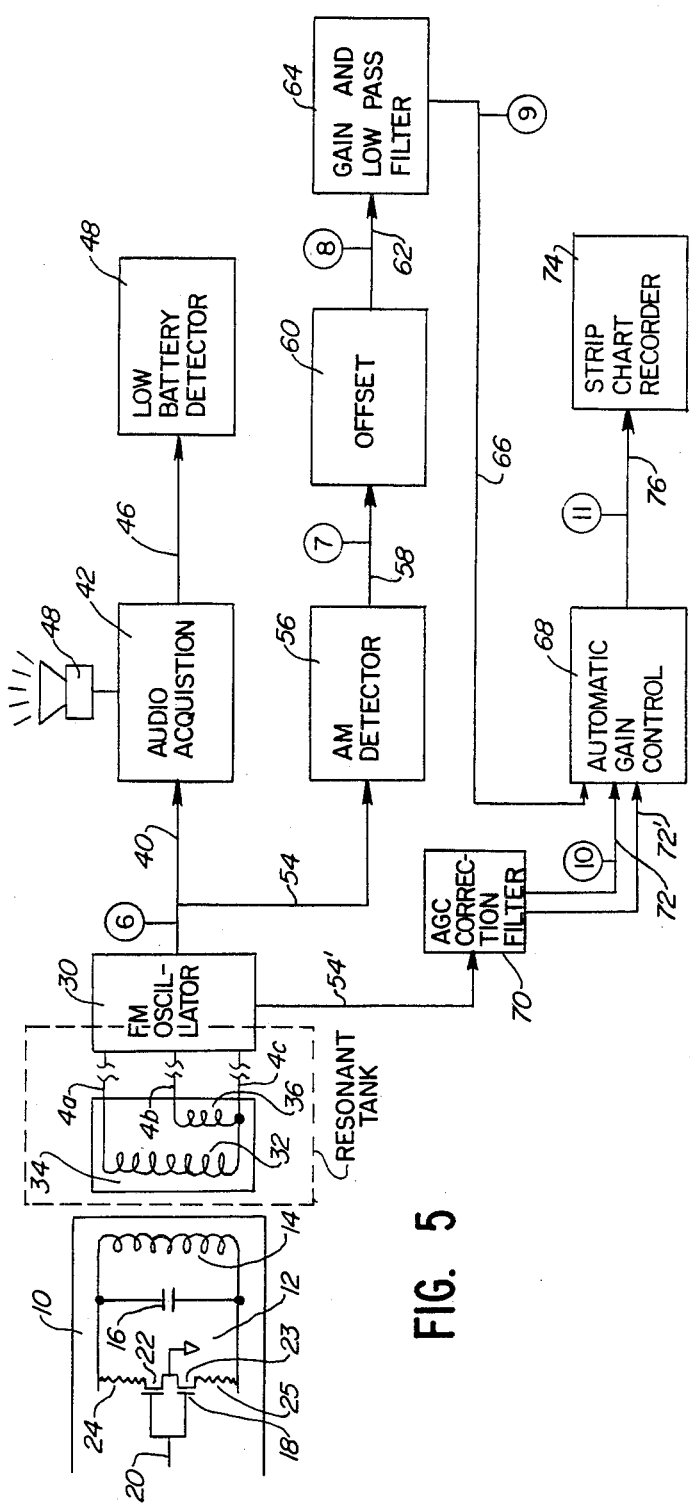
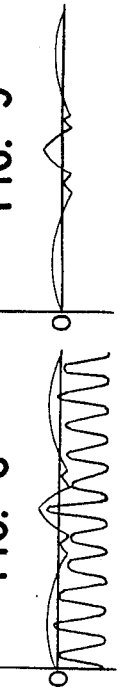
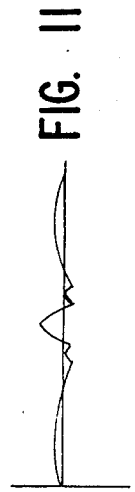
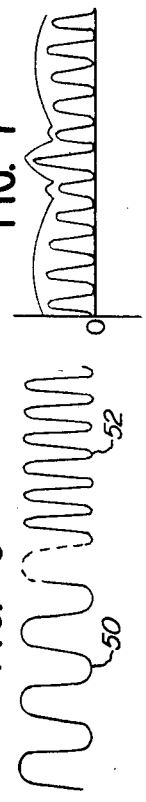
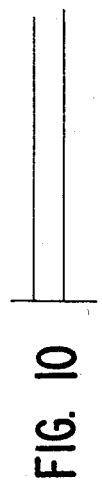
FIG. 5
FIG. 6
FIG. 7
FIG. 8
FIG. 9
FIG. 10
FIG. 11

IMPLANT COMMUNICATION SYSTEM WITH PATIENT COIL

BACKGROUND OF THE INVENTION

The present invention concerns a novel system for communicating with a tank circuit that is implanted in a patient, for example, a telemetry system for communicating with an implanted cardiac pacer.

In cardiac pacing there is typically communication between the implanted pacer and an external telemetry/programming unit. The external telemetry/programming unit generally comprises a console which contains appropriate circuitry and operator controls for communicating with the implanted pacer. In its telemetry mode, signals from the pacer are received by the circuitry within the external console and are detected. In its programming mode, signals are transmitted from the circuitry within the console and are received by the circuitry within the implant and are stored. The external console is typically a relatively large unit which may have a width of about 5 inches, a length of about 10 inches and a weight of about 5 pounds.

An example of one type of telemetry console, and its operation in communicating with an implanted cardiac pacer, is disclosed in U.S. Pat. No. 4,361,153, issued Nov. 30, 1982. It can be seen that the external console is placed on the patient's skin, overlying the implant, in as close proximity as possible to the implant. Because of the bulkiness and weight of the external console, the patient is generally required to lie down during the telemetry or programming procedure.

We have discovered a system for communicating with an implant in which the item in contact with the patient's skin and in proximity with the implant is extremely lightweight and small, thereby avoiding the difficulties concomitant with a bulky circuit console. Using the illustrative embodiment of our invention, the item which contacts the patient's skin externally can be manufactured with ease and economy, may be made sterilizable, may be disposable, may be flexible, may be constructed so that the patient may wear it for a period of time, and it affords a significant amount of latitude with respect to its placement on the patient.

Other objects and advantages of the present invention will become apparent as the description proceeds.

SUMMARY OF THE INVENTION

In accordance with the present invention, a novel system is provided for communicating with a tank circuit implanted in a patient. The system includes a telemetry circuit that is enclosed within a housing and including an oscillator. An inductor coil is located out of the housing for positioning externally on the patient in proximity to the implanted tank circuit. An electrical wire in the form of a flexible lead interconnects the inductor coil and the telemetry circuit. The inductor coil is operative, when electrically connected to the telemetry circuit, to form at least a portion of a resonant tank for the oscillator.

Thus the inductor coil, which may be referred to as the patient's coil, is separate from the telemetry circuit housing and the inductor coil may be formed as a flat coil in a relatively small configuration which is very lightweight.

In the illustrative embodiment, the inductor coil includes a primary winding and a secondary winding, with the primary winding operating as a transmission coil from the oscillator. The inductor coil has a generally disc shape, with one side thereof being adapted for contact with the patient's skin overlying the implanted tank circuit.

In a novel process as disclosed in this application, steps are provided for communicating with a tank circuit implanted in a patient. The steps comprise providing a telemetry circuit enclosed within a housing and including an oscillator, providing a separated inductor coil located outside of the housing and interconnected to the housing by electrical wire, and communicating with the implanted tank circuit by placing the inductor coil on the patient's skin in proximity to the implanted tank circuit and locating the separated housing at a remote position from the implanted tank circuit.

A more detailed explanation of the invention is provided in the following description and claims, and is illustrated in the accompanying drawings.

BRIEF DESCRIPTION OF THE DRAWINGS

FIG. 1 is a view of a patient using the system of the present invention; FIG. 2 is a front elevational view, partially broken, of an inductor coil used in connection with the present invention;

FIG. 3 is a cross-sectional view thereof, taken along the plane of the line 3—3 of FIG. 2;

FIG. 4 is a schematic diagram of the winding for the coil of FIGS. 2 and 3;

FIG. 5 is a block diagram of a telemetry system using the coil of FIGS. 2–4; and FIGS. 6–11 illustrate waveforms present on correspondingly numbered lines of FIG. 5.

DETAILED DESCRIPTION OF THE ILLUSTRATIVE EMBODIMENT

Referring to FIG. 1, a patient 2 is shown, having a telemetry/programming system comprising a housing and separated inductor coil (i.e., patient's coil) 32. Inductor coil 32 is affixed to the patient's skin and is coupled to housing 3 by means of a flexible electrical lead 4 having an electrical plug 5 (FIG. 2). Housing 3 contains all of the external programming and telemetry circuitry, such as the oscillator, battery power supply, detection circuitry, etc., except that the inductor coil 32, which forms the transmission or reception coil for the oscillator within housing 3, is separated from the housing. Coil 32 comprises a primary coil 34 preferably having 120 turns of No. 28 copper wire. A secondary coil 36, preferably comprising 20 turns of No. 28 copper wire, is wound concentrically about primary coil 34. Referring to FIG. 4, the ends of the windings 4a, 4b and 4c form flexible electrical lead 4. Coil 32 defines a central circular opening having a diameter of 1⅜ inches and the overall coil 32 is circular in configuration and is generally disc-shaped, with the circumference having a diameter of 3¼ inches and with the coil having a thickness of 0.040 inches. It is preferred that the coil have a diameter that is at least 50 times its thickness.

It is preferred that primary winding 34 and secondary winding 36 each have a thickness about three wire widths, with the wires having a thermoplastic coating so that they may be heated to form an integral unit. The coil is then pulled off the bobbin (on which it is wound) and encapsulated with an appropriate potting compound, such as a thermosetting potting material.

Inductor coil 32 is very lightweight and easy to manufacture. It can be manufactured with very wide tolerances, may be disposable and/or sterilizable. In the illustrative embodiment, both faces of inductor coil 32 are flat, so that the coil may be placed against the patient's skin and may be readily attached to the skin allowing the patient to sit upright or move about with the coil attached. Enough electrical lead 4 would be supplied so that the programmer/receiver console 3 is remote from the coil 32 and can be rested on the lap, a desk or otherwise carried about. The flat coil 32 is almost invisible under the clothing so it can be easily used for a technique in which it is carried on the skin coupled to a telemetry device or recorder for a substantial period of time.

It has been found that by utilizing the dimensions set forth above, there is a spherical electromagnetic field lobe produced that has a diameter of about 6 inches. In this manner, the patient has a great latitude in obtaining signals even if the coil 32 is not placed exactly in the proper position with respect to the implanted pacer.

Although no limitation is intended, the coil can be used with the system illustrated in FIG. 5. Referring to FIG. 5, an implant 10 is shown therein, including a tank circuit 12 comprising a tuned coil 14, a capacitor 16, and a shunt circuit 18 for varying the impedance of tank circuit 12 in accordance with an input data signal on line 20. Line 20 is connected to the common gates of a pair of FETs 22, 23, the sources of which are connected to the ground of implant 10 and the drains of which are connected, respectively to resistors 24 and 25.

An external programming and telemetry unit includes, among other things, an FM oscillator 30. The FM oscillator has the patient's coil 32, comprising a primary 34 and a secondary 36. The patient's coil 32 is wire coupled via flexible leads 4a–4e to the oscillator and the rest of the external unit. As stated above, in this manner, the patient's coil can be small and lightweight, and can be separated from the rest of the external unit by means of the wire, thereby allowing the patient's coil to be placed in a desired location overlying the implanted enclosure 10, with the remainder of the external unit separated therefrom.

Oscillator 30 is coupled via line 40 to audio acquisition circuit 42, which is connected to a speaker 44. Audio acquisition circuit 42 is coupled via line 46 to a low battery detector 48.

Oscillator 30 will provide a varying frequency in response to the positioning of coil 32 relative to coil 14 of implant 10. Referring to FIG. 6, the waveform from oscillator 30 is shown therein with the first portion 50 of the waveform having a particular frequency corresponding to the frequency generated by oscillator 30 when the patient's coil 32 is not in proximity to coil 14 of the implant 10. However, as patient's coil 32 approaches coil 14, the frequency will increase and portion 52 of the waveform of FIG. 6 illustrates the increased frequency waveform that is generated as a result of patient's coil 32 overlying the implant 10 and being in proximity with coil 14. Audio acquisition circuit 42, which receives this waveform, will indicate proximity of coil 32 with respect to coil 14 by issuing a sound from speaker 44 that is higher in pitch as proximity is increased. Other proximity indicia, such as the increased illumination of an LED or a light bulb, may alternatively be utilized.

Low battery detector 48, which is coupled to audio acquisition circuit 42, enables the operator or patient to determine if the battery in the external programming unit is too low for proper operation.

The FIG. 6 waveform generated by FM oscillator 30 is fed via line 54 to an AM detector 56 which cuts the carrier wave in half to effectively save the top half of the carrier wave. The output of AM detector 56 is illustrated in FIG. 7. This output is fed via line 58 to an offsetting gain circuit 60 which strips off the DC that is inherently developed by the AM detector. The output of offsetting gain circuit 60 is illustrated in FIG. 8. This output is fed via line 62 to a gain and low pass filter circuit 64 which is tuned to a cut off frequency of, for example, 250 hertz. The output of low pass filter 64 is illustrated in FIG. 9. This enables the message to be recovered from the waveform, and this message is fed via line 66 to automatic gain control circuit 68. Also fed to the automatic gain control circuit 68 is the DC representation of the distance of the patient coil 32 relative to implant coil 14. That signal passes through automatic gain control correction filter 70 and is fed via line 72 to automatic gain control circuit 68. The output of automatic gain control correction filter 70 on line 72 is illustrated in FIG. 10.

The purpose of using automatic gain control circuit 68 is so that a strip chart recorder 74, which is coupled via line 76 to the output of the gain control circuit 68, will have a corrected gain notwithstanding the particular position of the patient coil 32 with respect to implant 10. Otherwise, if patient coil 32 was at different distances, strip chart recorder 74 would receive different amplitude signals and operate erratically. The output of automatic gain control circuit 68, which is on line 76, is illustrated in FIG. 7, and it is this output which drives strip chart recorder 74 to provide a graphical recordation of the data signals. Strip chart recorder 74 may have an output jack for connecting the strip chart recorder to a telephone line for transmitting the message via telephone to a physician.

For additional information concerning the implanted tank circuit 12 and its telemetry operation, reference is hereby made to U.S. Pat. No. 4,361,153. Although the telemetry operation has been described, it is to be understood that this system may be used for programming. To this end, oscillator 30 would transmit carrier pulses instead of a continuous carrier signal. The carrier pulses would be outputted in response to programmed control by a microprocessor and the implant 10 would carry means for receiving and storing the program that is transmitted by the oscillator under the control of the microprocessor.

The frequency and the amplitude of the carrier on line 40 and line 54 will be responsive to the telemetry signals generated by the implanted tank circuit 12. The carrier frequency generated by oscillator 30 will also be responsive to the proximity of coil 34 to coil 14. Thus, as the impedance of the tank circuit 12 varies in response to the telemetry signals on line 20, this varying impedance will cause a variation in the frequency and the amplitude of the generated carrier signal from oscillator 30, which is detected and recorded.

It can be seen that a system has been shown and described in which a patient's coil is utilized, and is separated from the telemetry/programming unit, so that the patient can wear the coil comfortably. Further, the coil can be manufactured easily, it has an increased uniform telemetry field which exhibits no data reversal side lobes as seen in previous telemetry coils, and it may be sterilizable and disposable.

Although an illustrative embodiment of the invention has been shown and described, it is to be understood that various modifications and substitutions may be made by those skilled in the art without departing from the novel spirit and scope of the present invention.

What is claimed is:

1. A pacing system which comprises:
   an implantable pacer having a tank circuit contained therein;
   an external telemetry circuit for transmitting and receiving data to and from said pacer;
   said external telemetry circuit being enclosed within a housing and including a variable frequency oscillator having a portion of a resonant tank circuit;
   an inductor coil which forms another portion of said resonant tank circuit of said external telemetry circuit, said inductor coil being located outside of said housing for positioning externally on the patient in proximity to the implanted tank circuit;
   electrical wire interconnecting the inductor coil and the enclosed telemetry circuit;
   said variable frequency oscillator having means for generating a waveform that is frequency-responsive to the telemetry signals provided by the implanted tank circuit.

2. A system as described in claim 1, said inductor coil including a primary winding operating as a transmission coil from the oscillator to the implanted tank circuit.

3. A system as described in claim 1, said inductor coil having a generally disc shape, with one side thereof being flat whereby it is adapted for contact with the patient's skin overlying the implanted tank circuit.

4. A system as described in claim 1, said inductor coil having a flat side that is adapted for contact with the patient's skin overlying the implanted tank circuit.

5. A system as described in claim 3, including a plastic potting compound encapsulating said inductor coil.

6. A system as described in claim 1, said inductor coil having a circular configuration, and being generally disc-shaped, with a diameter that is at least 50 times its thickness.

7. A system as described in claim 6, including a plastic potting compound encapsulating said inductor coil.

8. A system as described in claim 6, in which said inductor coil has a diameter of approximately 3⅛ inches and a thickness of approximately 0.04 inches.

9. A system as described in claim 6, said inductor coil defining a central opening.

10. A pacing system which comprises:
    an implantable pacer having a tank circuit contained therein;
    an external telemetry circuit for transmitting and receiving data to and from said pacer;
    said external telemetry circuit being enclosed within a housing and including a variable frequency oscillator having a portion of a resonant tank circuit;
    an inductor coil which forms another portion of said resonant tank circuit of said external telemetry circuit, said inductor coil being located outside of said housing for positioning externally on the patient in proximity to the implanted tank circuit;
    said inductor coil including a primary winding operating as a transmission coil from the oscillator to the implanted tank circuit;
    said inductor coil having circular configuration, and being generally disc-shaped, with a diameter that is at least 50 times its thickness;
    electrical wire interconnecting the inductor coil and the enclosed telemetry circuit;
    said variable frequency oscillator having means for generating a waveform that is frequency-responsive to the telemetry signals provided by the implanted circuit.

11. A process for communicating with the tank circuit implanted in a patient, which comprises the steps of:
    providing an implantable pacer having a tank circuit contained therein;
    providing an external telemetry circuit for transmitting and receiving data to and from said pacer;
    said external telemetry circuit being enclosed within a housing and including a variable frequency oscillator having a portion of a resonant tank circuit;
    providing a separated inductor coil which forms another portion of said resonant tank circuit of said external telemetry circuit, said inductor coil being located outside of the housing and interconnected to the housing by electrical wire;
    providing the inductor coil with a primary coil operating as a transmission coil to transmit the signal generated by the oscillator to the implanted tank circuit;
    communicating with the implanted tank circuit by placing the inductor coil on the patient's skin in proximity to the implanted tank circuit and locating the separated housing at a remote position from the implanted tank circuit; and
    providing said variable frequency oscillator with means for generating a waveform that is frequency-responsive to the telemetry signals provided by the implanted tank circuit.

* * * * *